May 22, 1951 H. ROBINSON Plant Pat. 1,012
ROSE PLANT
Filed May 16, 1950
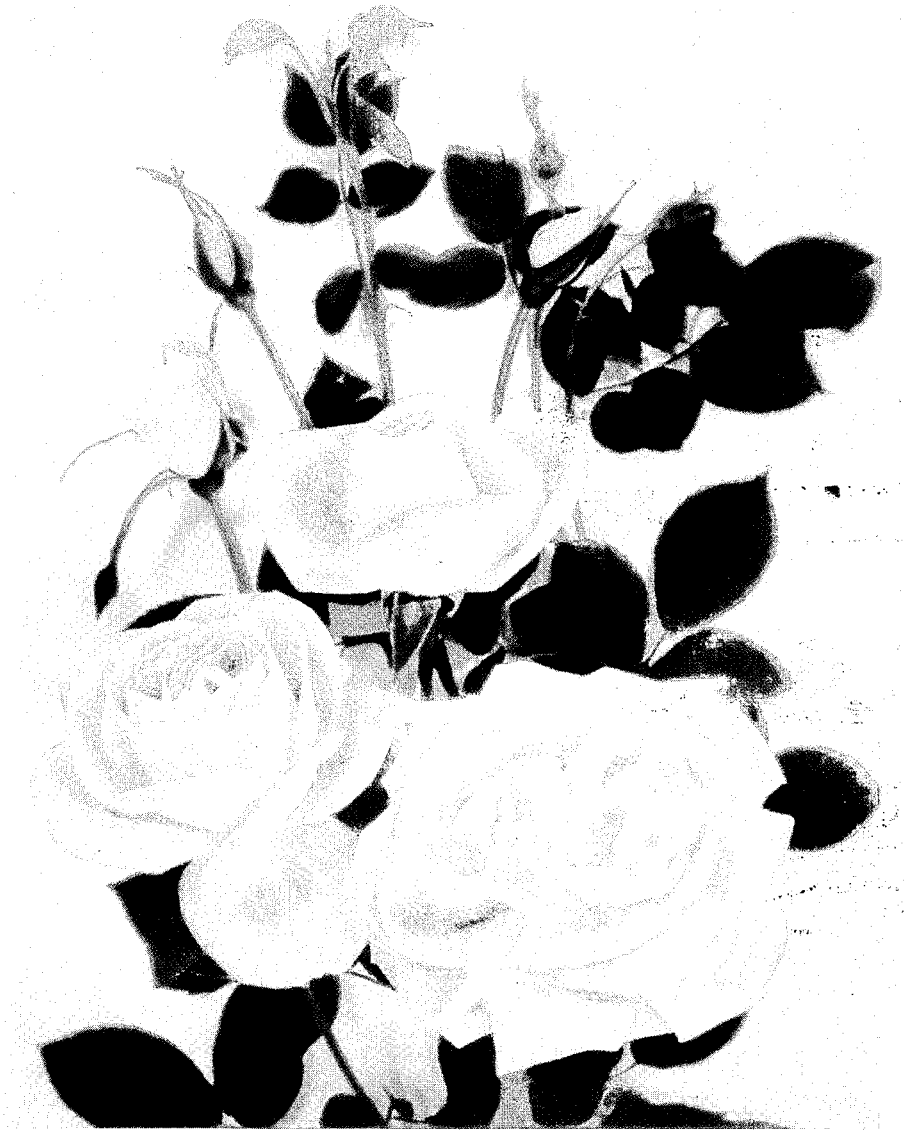
Inventor
Herbert Robinson
By Robert Cook
Attorneys.

Patented May 22, 1951

Plant Pat. 1,012

UNITED STATES PATENT OFFICE 1,012

ROSE PLANT

Herbert Robinson, Burbage, Hinckley, England, assignor to Jackson & Perkins Company, Newark, N. Y., a corporation of New York Application May 16, 1950, Serial No. 162,188

1 Claim. (Cl. 47—61)

The present invention relates to a new and distinct variety of rose plant of the hybrid tea class, originated by crossing a seedling of the variety "The Queen Alexandra" Rose (unpatented) × "Crimson Glory" (Plant Patent No. 105).

The latter of the above parent varieties is outstanding for its very vigorous habit of growth and by its resistance to disease.

The primary objective in making this cross was to retain the attractive and very fine color effect of "The Queen Alexandra" rose and improve the vigor and disease resistance of the plants of this variety. This objective was fully attained, as evidenced by the following novel combination of dominant characteristics which distinguish this new variety from its parents, as well as from any other variety of this class:

(1) The vigorous habit of the plant;

(2) The improved resistance to blackspot and mildew;

(3) The glossy and very attractive foliage;

(4) The rich contrast of color evident from the half-open bud to the full-blown flower;

(5) The red tones of the inside of the petals and the yellow tones on the reverse of the petals;

(6) The frequency of bloom and its persistence throughout the summer months.

Asexual reproduction of the new variety by budding at Newark, New York and at Pleasanton, California, shows that the foregoing characteristics come true to form and are established and transmitted through succeeding propagations.

The accompanying drawing illustrates specimens of the new variety, with the flowers in different stages of development from small bud to full-open bloom.

The following is a detailed description of the new variety, with color terminology in accordance with Ridgway's Color Standards and Nomenclature:

Parentage: Seedlings.

*Seed parent.*—Seedling of "The Queen Alexandra" Rose.

*Pollen parent.*—"Crimson Glory" (Plant Patent No. 105).

Classification: Botanic and commercial—hybrid tea.

*Flower*

(Observations made in the field at Newark, New York, in the morning of September 27, 1949.)

Blooming habit: Recurrent—continuous.

Bud:

*Size.*—Medium.

*Form.*—Ovoid. Is not affected by wet or hot weather.

*Color.*—When sepals first divide—Spectrum Red, Plate 1. When petals begin to unfurl—Light Orange Yellow, Plate 3, lightly overcast with Spectrum Red, Plate 1. When half-blown—inside of petals—Rose Red, Plate 12, lightly overcast with Tyrian Rose, Plate 2; reverse of petals—Light Orange Yellow, Plate 3.

*Sepals.*—Slightly branched. Curl back when petals begin to unfurl. Color—inside—Kildare Green, Plate 31; outside—Parrot Green, Plate 6.

*Calyx.*—Shape — apple. Size — large. Odor when rubbed—none. Color—Parrot Green, Plate 6.

*Peduncle.* — Length — medium. Aspect—smooth. Color—Kildare Green, Plate 31. Strength—erect; heavy.

*Opening.*—Bud opens up well. Is not affected by adverse weather conditions.

Bloom:

*Size.*—Very large. Average size when fully expanded, 5½ inches.

*Borne.*—Singly, and sometimes several to a stem.

*Stems.*—Medium length and strong.

*Form.*—When first open—cupped. Permanence—retains its form to the end.

*Petalage.*—Double (full but open center). Number of petals under normal conditions, 35–40.

*Color.*—Center of flower—Rose Red, Plate 12—center petals furled in center showing Light Orange Yellow on reverse, Plate 3. Outer petals—Tyrian Rose, Plate 12, lightly overcast with Rose Red, Plate 12. Base of petals—Empire Yellow, Plate 12. Inside of petals—Rose Red, Plate 12. Reverse of petals—Buff Yellow, Plate 4, suffused with Thulite Pink, Plate 26. General tonality from a distance—Rose Red, Plate 12.

*Discoloration.*—General tonality at end of first day—Rose Red, Plate 12. Second day—Tyrian Rose, Plate 12, overcast with Rose Red, Plate 12. Third day—Tyrian Rose, Plate 12, lightly overcast with Rose Red, Plate 12.

Petals:

*Texture.*—Thick. Are not affected by wet or hot weather.

*Appearance.*—Inside—satiny; outside—shiny.

*Form.*—Round.

*Arrangement.*—Formal (with "rags" in center). Petaloids in center—many and large.

*Persistence.*—Drop off cleanly.

*Fragrance.*—Slight. Nature—tea (average hybrid tea scent).

*Lasting quality.*—On the plant and as cut flower—long.

Genital organs:

*Stamens, anthers.*—Large, many. Color—Apricot Yellow, Plate 4. Arrangement—regular around styles.

*Stamens, filaments* (threads).—Long. Color—Lemon Chrome, Plate 4.

*Pollen.*—Color—Pinard Yellow, Plate 4.

*Styles.*—Loosely separated, uneven length. Medium length, thin.

*Stigmas.*—Color—Baryta Yellow, Plate 4.

*Ovaries.*—All enclosed in calyx.

*Plant*

Form: Bush.

Growth: Vigorous, upright.

Foliage: 5 to 7 leaflets.

*Size.*—Medium.

*Quantity.*—Abundant.

*Color.*—New foliage: upper side—Yellowish Oil Green, Plate 5; serrations—Victoria Lake, Plate 1; under side—Absinthe Green, Plate 31, overcast with Victoria Lake, Plate 1. Old foliage: upper side—Dark Cress Green, Plate 31; under side—Light Cress Green, Plate 31.

*Shape.*—Oval.

*Texture.*—Upper side—glossy; under side—smooth. Ribs and veins—ordinary.

*Edge.*—Serrated (saw toothed).

*Serration.*—Single, small.

*Leaf stem.*—Color—Rainette Green, Plate 31. Under side—prickles.

*Stipules.*—Medium length, smooth.

*Disease resistance.*—Resistant.

Wood:

*New wood.*—Color—Nopal Red, Plate 1. Bark—smooth.

*Old wood.*—Color—Cress Green, Plate 31. Bark—smooth.

Thorns:

*Thorns.*—Quantity—on main stalks from base and on laterals from stalk—ordinary. Form—narrow base, medium length, hooked downward. Color when young—Nopal Red, Plate 1. Position—irregular.

*Prickles.*—Quantity—on main stalks and on laterals—few. Color—Rainette Green, Plate 31.

*Short needles.*—Quantity—on main stalks and on laterals—few.

I claim:

A new and distinct variety of rose plant of the hybrid tea class, characterized as to novelty by the vigorous habit of the plant and its resistance to blackspot and mildew, by its glossy and attractive foliage, by the rich contrast of color evident from the half-open bud to the full-blown flower, with red tones on the inside of the petals and yellow tones on the reverse of the petals, and by the frequency of bloom and its persistence throughout the summer months, substantially as shown and described.

HERBERT ROBINSON.

No references cited.